United States Patent [19]

Short et al.

[11] 4,361,715

[45] Nov. 30, 1982

[54] OLEFINS

[75] Inventors: Glyn D. Short, Yarm; Michael S. Spencer, Stockton-on-Tees; Thomas V. Whittam, Darlington, all of England

[73] Assignee: Imperial Chemical Industries Limited, London, England

[21] Appl. No.: 260,838

[22] Filed: May 15, 1981

[30] Foreign Application Priority Data

May 13, 1980 [GB] United Kingdom ................ 8015888

[51] Int. Cl.$^3$ .............................................. C07C 1/20
[52] U.S. Cl. .................................................. 585/640
[58] Field of Search ........................................ 585/640

[56] References Cited

U.S. PATENT DOCUMENTS 4,172,856 10/1979 Spencer et al. ..................... 585/640

FOREIGN PATENT DOCUMENTS 6501 1/1980 European Pat. Off. ............ 585/640
2061999 5/1981 United Kingdom ................ 585/640

Primary Examiner—Curtis R. Davis
Attorney, Agent, or Firm—Cushman, Darby & Cushman

[57] ABSTRACT

A feedstock comprising a hydrocarbon containing 2 or more carbon atoms in the molecule and/or a hydrocarbon derivative containing hydrogen-carbon links is converted to olefins over the zeolite NU-3. When in particular the feedstock is methanol or dimethyl ether olefins are formed with high selectivity against formation of aromatics.

6 Claims, No Drawings

OLEFINS

This invention relates to olefins and in particular to a process of making them by conversion of hydrocarbons and/or their derivatives in the presence of zeolite NU-3 as catalyst.

Olefins, especially ethylene and propylene, are used on a large scale as intermediates for the manufacture of staple products such as olefin polymers, ethylene oxide, non-ionic detergents, glycols and fibre-forming polyesters. Processes for producing olefins usually involve non-catalytic pyrolysis of volatile hydrocarbons such as natural gas liquids or petroleum distillates. Catalytic pyrolysis processes have been proposed but do not appear to have reached industrial use.

In countries where such volatile hydrocarbons are not to be used but such feedstocks as coal, oil shale and methane, and consequently carbon monoxide/hydrogen synthesis gas derived therefrom, are available, it would be desirable to produce olefins from synthesis gas. It has been proposed to do this by converting the synthesis gas to methanol or to hydrocarbons and/or their oxygenated derivatives and reacting such products over a zeolite of the ZSM-5 family. The reaction over such a zeolite is not entirely satisfactory because the olefins tend to react further to produce aromatic hydrocarbons, including polymethylated benzenes of limited usefulness. Better conversions to olefins can apparently be achieved by using a modified catalyst and/or by careful temperature control, but such measures increase the complexity and cost of the process.

We have now found that our recently discovered zeolite NU-3 can catalyse the conversion of such feedstocks to olefins with only slight, if any, formation of aromatic compounds and only slow deactivation of the catalyst.

The invention provides a process for making an olefin containing 6 or fewer carbon atoms in the molecule by reacting over a catalyst a feedstock comprising a hydrocarbon containing 2 or more carbon atoms in the molecule and/or a hydrocarbon derivative containing hydrogen-carbon links and recovering the olefin from the product of the reaction, characterised in that the catalyst comprises zeolite NU-3 as hereinafter defined.

Zeolite NU-3 has a molar chemical composition represented by the formula.

0.5 to $1.5R_2O.Y_2O_3$ . at least $5XO_2$. 0 to $400H_2O$ where R is a monovalent cation or $1/n$ of a cation of valency n, x is silicon and/or germanium, Y is one or more of aluminium, gallium and iron and $H_2O$ is water of hydration additional to water notionally present when R is H. Zeolite NU-3 has an X-ray diffraction pattern including the characteristic lines set out in Table 1 (as determined by standard technique using copper K alpha radiation). More particularly Table 2 shows X-ray data for sodium N-methyl quinuclidinium Nu-3 as prepared, and Table 3 for its calcined Na-H form. The X-ray pattern is affected in minor ways by the type of cation present, but there are greater changes in relative intensities on burning out organic cations. No further changes occur on preparing hydrogen forms of NU-3 from Na-H NU-3.

Within the above definition of chemical composition the number of mols of $XO_2$ is typically in the range 5 to 1000 and zeolite NU-3 appears to be most readily formed in a state of high purity when the number of mols of $XO_2$ is in the range 10 to 300. Preferably there is at last 0.8 mol of $R_2O$ per $Al_2O_3$. Preferably X is silicon and Y is aluminium.

Our co-pending UK application 8015890 of May 13, 1980 describes in more detail NU-3 and its method of preparation, particularly the synthesis thereof in a reaction mixture comprising quinuclidinium ions.

In order to be useful to a preferred extent in the process of the invention, NU-3 is converted from the form in which it is hydrothermally produced, in which form it contains the oxides e.g. of alkali metal and of quinuclidinium or of a degradation product thereof, to an active form by ion exchange of at least part of the ions represented by the alkali metal oxide and preferably also subjected to removal of at least part of the quinuclidinium,

TABLE 1

Typical X-ray diffraction intensities for zeolite NU-3

| d(A) | I | d(A) | I | d(A) | I |
|---|---|---|---|---|---|
| 11.3 ± 0.2 | W | 4.42 ± 0.08 | W | 3.12 ± 0.05 | S |
| 10.1 ± 0.2 | W - M | 4.32 ± 0.08 | W - M | 3.03 ± 0.05 | W |
| 8.0 ± 0.14 | M - VS | 4.21 ± 0.08 | S - VS | 2.98 ± 0.05 | W - M |
| 7.65 ± 0.14 | W - M | 4.02 ± 0.07 | VS | 2.81 ± 0.05 | W |
| 6.56 ± 0.14 | W - VS | 3.95 ± 0.07 | W | 2.75 ± 0.05 | M - S |
| 5.71 ± 0.12 | W | 3.80 ± 0.07 | M - S | 2.59 ± 0.04 | W |
| 5.54 ± 0.1 | W | 3.77 ± 0.06 | W - M | 2.50 ± 0.03 | W |
| 5.09 ± 0.1 | M - VS | 3.66 ± 0.06 | W - M | 2.07 ± 0.03 | W |
| 4.97 ± 0.09 | W | 3.54 ± 0.06 | W | 2.01 ± 0.03 | W |
| 4.75 ± 0.08 | W | 3.42 ± 0.06 | W - M | 1.90 ± 0.02 | W |
| 4.66 ± 0.08 | W | 3.28 ± 0.05 | W - M | 1.86 ± 0.02 | W |
| 4.61 ± 0.08 | W - S | 3.18 ± 0.05 | W | | |

Key:
VS (very strong) = $I/Io \times 100$ of 60-100
S (strong) = $I/Io \times 100$ of 40-60
M (medium) = $I/Io \times 100$ of 20-40
W (weak) = $I/Io \times 100$ of 0-20

TABLE 2

Zeolite NU-3 as freshly prepared

| d(A) | 100 I/Io | d(A) | 100 I/Io |
|---|---|---|---|
| 10.11 | 8 | 4.21 | 56 |
| 8.01 | 33 | 4.01 | 100 |
| 7.56 | 1 | 3.78 | 35 |
| 6.56 | 19 | 3.54 | 6 |
| 5.50 | 10 | 3.42 | 3 |
| 5.07 | 79 | 3.27 | 18 |
| 4.94 | 14 | 3.18 | 2 |
| 4.69 | 6 | 3.12 | 48 |
| 4.62 | 2 | 3.03 | 9 |
| 4.39 | 3.5 | 2.81 | 5 |
| 4.25 | 12 | 2.75 | 38 |

TABLE 3

Zeolite NU-3 in calcined Na-H form

| d(A) | 100 I/Io | d(A) | 100 I/Io |
|---|---|---|---|
| 10.10 | 21 | 4.21 | 49 |
| 8.03 | 100 | 4.01 | 85 |
| 7.55 | 8 | 3.78 | 22 |
| 6.58 | 75 | 3.54 | 11 |
| 5.51 | 3 | 3.42 | 6 |
| 5.07 | 40 | 3.28 | 22 |
| 4.94 | 2 | 3.18 | 0 |
| 4.69 | 0 | 3.12 | 51 |
| 4.62 | 1 | 3.03 | 11 |
| 4.39 | 0 | 2.81 | 8 |
| 4.24 | 14 | 2.75 | 42 | for example, by calcination in air. The alkali metal is replaced to the extent of at least 10% of the acid sites, preferably at least 50%, for use in the process of the invention. The alkali metal compound content can be less than 4000, especially less than 500 ppm w/w calculated as equivalent $Na_2O$ on a water-free basis. The quinuclidinium content is preferably less than 2% w/w calculated as elemental carbon. Preferably the NU-3 is activated by heating at 400°–600° C. in air or oxygen-free gas before beginning the reaction; such treatment is also suitable for re-activating used catalyst. The water content of freshly activated or reactivated catalyst is preferably 0 to 2 mols in the above chemical composition formula.

In the active form the alkali metal ions have been replaced at least partly by hydrogen or ions of polyvalent metals. Replacement by hydrogen can be effected by exchange with acid or with ions of ammonium or non-quaternary amine, since such ions decompose on calcination to leave hydrogen ions. The polyvalent metal is preferably selected from those having little or no catalytic activity for hydrogenation, except when synthesis is to accompany conversion, as described below. Suitable metals are from Group II, III (including rare earths) and VII of the Periodic Table as set out in "Abridgments of Specifications" published by the UK Patent Office. Of them, zinc, manganese—II and aluminium, alone or in mixtures, are especially preferred. Preferably hydrogen ions and polyvalent ions are both present. By such ion exchanges it is possible to make NU-3 varieties having increased stability, modified catalytic activity, modified product selectivity or decreased coking tendency or more than one of such advantages when used in the process of the invention.

NU-3 may be used at full strength or in mixture with diluent material such as inert silica, alumina or clay, a suitable proportion of diluent being in the range 10–40%. The diluent may facilitate forming NU-3 into shapes (such as 1–10 mm cylinders or spheres for use in a fixed bed or into fine particles for use in a fluidised bed) and also enable the rates of the wanted and unwanted reactions over it to be controlled. The diluent can, if desired, be a zeolite. The invention includes also the process when carried out over varieties of NU-3 modified by treatment with a compound of one or more of boron, silicon, phosphorus, arsenic or antimony, or by partial coking or by calcination with or without steam, or more than one of such treatments.

The feedstock can be for example a normally gaseous (up to $C_4$) hydrocarbon or mixture such as LPG or a readily vaporisable hydrocarbon or mixture such as natural gas liquids or naphtha. If higher hydrocarbons are to be reacted over NU-3, they are preferably first cracked, in a preliminary or concurrent step. If the feedstock is a hydrocarbon derivative it is suitably one having at least 2 hydrogen atoms linked to at least some of its carbon atoms. Oxygenated hydrocarbons such as alcohols, ethers, carboxylic acids, esters, aldehydes and ketones and their acetals are very suitable feedstocks. An especially useful application of the process is the production of olefins from methanol and/or dimethyl ether, since NU-3, unlike for example the ZSM-5 family of zeolites, appears to be selective for the production of normally gaseous olefins and against the production of armatic hydrocarbons. Crude feed and/or waste streams containing organic sulphur or nitrogen compounds can be upgraded to useful products by the process of the invention.

The products leaving the NU-3 catalyst may include hydrocarbons other than the required olefins, as well as unwanted hydrocarbon derivatives and possibly also unconverted feedstock. The crude product is separated by condensation of any normally liquid compounds in it and the gaseous fraction is resolved by distillative fractionation or by adsorption. Unwanted and unreacted materials, after recovery of the required olefins and separation of products such as methane, carbon oxides, water and (when appropriate) hydrogen, can be subjected to further stages of conversion over NU-3 or recycled for further conversion with the main feedstock or to synthesis gas.

The reaction temperature is suitably in the range 300–600, especially up to 500°, for example 350°–450° C.

The pressure at which the process is carried out is suitably in the range 1–50 atm. abs., especially 1–15 atm. abs., but higher pressures for example to 300 atm. abs. can be used if convenient, for example as described below when synthesis is combined with the process of the invention.

The space velocity should be controlled so as to give the required product distribution. Thus, for example, when the feedstock is methanol, reaction at a liquid hourly space velocity of about 1.0 produces a high proportion of dimethyl ether than when the space velocity is 0.2. The dimethyl ether can be recycled or reacted in a separate bed of NU-3 or other catalyst.

The catalyst maintains its activity for a substantial period, but can be regenerated by heating in the conditions preferably used for activating it. Very suitably it is used in the form of a fluidised bed and catalyst is continuously withdrawn, passed through a regeneration zone and returned to the olefinforming reaction.

The process of the invention can be used in combination with a process of synthesis of hydrocarbons and/or oxygenated hydrocarbons by catalytic reaction of carbon oxides with hydrogen. Synthesis products can be separated before the reaction over NU-3 but, if desired, the NU-3 can be disposed so as to act on the synthesis products in advance of any product separation step, for example in a bed downstream of the synthesis catalyst, or by using a mixture of discrete pieces of synthesis catalyst and NU-3 catalyst, or by using discrete pieces made by shaping a mixture of powdered NU-3 and synthesis catalysts or by applying to NU-3 by impregnation or ion-exchange one or more compounds of metals or oxides having such synthesis activity. Suitable synthesis catalysts contain for example one or more of copper, zinc oxide, chromium oxide and the non-noble or noble metals from Group VIII of the Periodic Table. The pressure of the reaction over NU-3 can be chosen to suit the conditions of the synthesis reaction.

EXAMPLE 1

Preparation of sodium N-methyl quinuclidinium (Q) NU-3

The synthesis mixture had the following molar composition 11.5 $Na_2O$.17.1 $QI.Al_2O_3$.60 $SiO_2$. 600 $H_2O$. Solid silica (111 g of the product AKZO KS 300, of composition 7.18 $Na_2O.Al_2O_3$. 695 $SiO_2$ .226 $H_2O$) were dispersed in 311.6 g of an aqueous solution containing 22 g sodium hydroxide and 5.6 g sodium aluminate (1.25 $Na_2O$. $Al_2O_3$.3 $H_2O$). The resulting slurry was heated to 95° C. with stirring and then 120 g of N-methylquinuclidinium iodide were added with stirring. The resulting gel was reacted with stirring in a 1-liter stainless steel autoclave for 3 days at 180° C. The slurry was filtered, washed twice with 1 liter of distilled water at 60° C., and then dried overnight at 120° C. The product was sodium N-methyl quinuclidinium NU-3 having the X-ray diffraction data shown in Table 2, and a molar composition 0.3 $Na_2O$.1.5 $Q_2O.Al_2O_3$.45 $SiO_2$. 15

$H_2O$. A sample of it was calcined in air (saturated with water at 25° C.) for 48 hours at 450° C. The resulting sodium hydrogen NU-3 had the X-ray data shown in Table 3. The calcined NU-3 was slurry exchanged with 5 ml N.HCl per g of zeolite for 1 hour at 25° C. and was then washed twice with 10 ml distilled water per g of zeolite. Finally the product was dried overnight at 120° C. and calcined at 450° C. in air for three hours. This hydrogen NU-3 had an X-ray diffraction pattern identical with that of sodium hydrogen NU-3 and had the following molar composition ignoring hydrogen 0.01 $Na_2O.Al_2O_3.46\ SiO_2$.

Conversion of methanol

A sample of H-NU-3 from Example 1 was tested as an acid catalyst in the conversion of methanol. A bed of about 0.3 ml of 3 mm pellets was activated at 450° C. for 3 hours in a nitrogen stream. It was maintained at 450° C. and a sample of methanol (0.6 ml) was injected above it. The $C_1$-$C_4$ hydrocarbon analysis of the products is given in Table 4. There was no significant production of aromatics.

TABLE 4

|  | % v/v |  |
|---|---|---|
| methane | | 19.8 |
| ethane | | 0.6 |
| ethene | | 22.7 |
| propane | | 9.0 |
| propene | | 38.6 |
| i-butane | under | 0.1 |
| n-butane | | 0.4 |
| butene-1 | | 2.4 |
| iso-butene | | 2.9 |
| trans butene-2 | | 2.7 |
| cis butene-2 | | 1.0 |

EXAMPLE 2

Conversion of undiluted methanol

In a continuous flow apparatus a 10 ml bed of 3 mm pellets (5.6 g) of the H-NU-3 was activated for 16 hours at 450° C. in a stream of nitrogen. It was kept at 450° C. and methanol vapour passed through at a liquid hourly space velocity (LHSV) of 1.12 vol. feed/vol. catalyst/hour. The $C_1$-$C_4$ hydrocarbon analysis given in Table 5. No liquid hydrocarbons were formed.

The liquid product consisted of water, unconverted methanol and dimethyl ether. The conversion of methanol to hydrocarbon was about 50% in the first hour of the run and about 35% in the second hour. High yields of olefins were obtained throughout the run. The yields of total olefins and of ethene both increased during the run.

TABLE 5

| Time after start (min) | | 7 | 55 | 109 |
|---|---|---|---|---|
| % v/v | methane | 17.9 | 18.1 | 15.8 |
| | ethane | 20.4 | 4.6 | 2.9 |
| | ethene | 22.1 | 40.0 | 48.9 |
| | propane | 11.3 | 3.6 | 0.3 |
| | propene | 19.6 | 25.0 | 25.3 |
| | i-butane | <0.1 | <0.1 | 0 |
| | n-butane | 0.4 | <0.1 | <0.1 |

TABLE 5-continued

| Time after start (min) | 7 | 55 | 109 |
|---|---|---|---|
| butene-1 | 1.3 | 2.8 | 1.6 |
| i-butene | 4.2 | 1.8 | 1.8 |
| trans-butene-2 | 2.9 | 2.7 | 2.6 |
| cis-butene-2 | <0.1 | 1.2 | 0.8 |
| total butenes | 8.4 | 8.5 | 8.5 |
| total olefins | 48.4 | 73.5 | 81.0 |

EXAMPLE 3

Example 2 was repeated at lower values of LHSV. Before each run the catalyst was re-activated by calcination in air for 16 hours at 450° C. The $C_1$-$C_4$ hydrocarbon analysis is given in Table 6. No liquid hydrocarbons were formed.

TABLE 6

| LHSV | | 0.66 | | | 0.34 | |
|---|---|---|---|---|---|---|
| Time after start (min) | | 48 | 95 | 141 | 48 | 106 |
| % v/v | methane | 23.2 | 15.7 | 23.7 | 21.1 | 18.0 |
| | ethane | 5.9 | 5.0 | 5.0 | 4.7 | 2.0 |
| | ethene | 31.0 | 45.7 | 38.7 | 45.0 | 44.7 |
| | propane | 5.8 | 2.3 | 0.2 | 0.9 | 0.8 |
| | propene | 24.4 | 23.1 | 22.2 | 19.6 | 25.3 |
| | i-butane | <0.1 | <0.1 | <0.1 | <0.1 | <0.1 |
| | n-butane | 0.1 | <0.1 | <0.1 | 0.2 | 0.3 |
| | butene-1 | 3.0 | 2.6 | 1.7 | 2.7 | 3.8 |
| | i-butene | 2.2 | 1.7 | 3.0 | 2.1 | 1.2 |
| | trans-butene-2 | 3.2 | 2.8 | 4.5 | 3.2 | 2.5 |
| | cis-butene-2 | 1.2 | 1.1 | 1.0 | 1.1 | 0.8 |
| | total butenes | 9.6 | 8.2 | 10.2 | 9.1 | 8.3 |
| | total olefins | 65.0 | 77.0 | 71.1 | 62.2 | 78.1 |

EXAMPLE 4

Example 2 was repeated at 350° C. Before the run the catalyst was re-activated by calcination in air for 16 hours at 450° C. The $C_1$-$C_4$ hydrocarbon analysis is given in Table 7. No liquid hydrocarbons were formed. As at 450° C., high yields of olefin were obtained. Ethene yields increased during the run. Butene yields were lower than in the runs at 450° C.

TABLE 7

| Time after start (min) | | 48 | 95 | 160 |
|---|---|---|---|---|
| % v/v | methane | 19.9 | 17.0 | 12.8 |
| | ethane | 4.2 | 6.8 | 3.9 |
| | ethene | 38.5 | 40.3 | 41.7 |
| | propane | 8.9 | 0.6 | <0.1 |
| | propene | 23.1 | 32.4 | 36.7 |
| | i-butane | <0.1 | <0.1 | <0.1 |
| | n-butane | 0.1 | <0.1 | <0.1 |
| | butene-1 | 1.8 | 1.1 | 1.7 |
| | i-butene | 0.7 | <0.1 | 0.6 |
| | trans-butene-2 | 2.1 | 0.9 | 1.9 |
| | cis-butene-2 | 0.6 | 0.6 | 0.6 |
| | total butenes | 5.2 | 2.6 | 4.8 |
| | total olefins | 66.8 | 75.3 | 83.2 |

EXAMPLE 5

Example 2 was repeated at 400° C. and at various values of LHSV. Before each run the catalyst was re-activated by calination in air for 16 hours at 450° C. The $C_1$-$C_4$ hydrocarbon analysis is given in Table 8. High yields of olefins, especially ethene, were obtained.

TABLE 8

| LHSV | 0.54 | | | 0.84 | | | 0.57 | | |
|---|---|---|---|---|---|---|---|---|---|
| Time after start (min) | 48 | 92 | 138 | 48 | 95 | 168 | 58 | 103 | 147 |
| % v/v | | | | | | | | | |
| methane | 22.8 | 12.7 | 11.2 | 18.6 | 11.2 | 9.7 | 21.0 | 11.8 | 10.5 |
| ethane | 6.6 | 5.5 | 4.0 | 5.7 | 4.5 | 2.2 | 6.3 | 5.0 | 4.2 |
| ethene | 30.6 | 43.5 | 44.6 | 38.2 | 46.6 | 40.5 | 26.6 | 47.4 | 46.0 |
| propane | 8.2 | 3.3 | 1.3 | 6.2 | 1.2 | 0.4 | 9.2 | 3.2 | 1.4 |
| propene | 22.5 | 26.3 | 33.0 | 22.6 | 29.9 | 37.2 | 25.0 | 25.0 | 31.6 |
| i-butane | <0.1 | <0.1 | <0.1 | <0.1 | <0.1 | <0.1 | <0.1 | <0.1 | <0.1 |
| n-butane | 0.2 | 0.3 | <0.1 | 0.3 | <0.1 | <0.1 | 0.7 | 0.1 | <0.1 |
| butene-1 | 2.7 | 3.8 | 2.0 | 2.6 | 2.1 | 6.7 | 3.0 | 2.8 | 2.5 |
| i-butene | 2.1 | 1.2 | 1.0 | 1.8 | 1.0 | 0.7 | 2.7 | 1.3 | 1.1 |
| t-butene-2 | 3.2 | 2.5 | 2.3 | 3.0 | 2.6 | 2.2 | 4.0 | 2.5 | 2.2 |
| c-butene-2 | 1.1 | 0.8 | 0.7 | 1.0 | 1.0 | 0.4 | 1.5 | 0.9 | 0.6 |
| total butenes | 9.1 | 8.3 | 6.0 | 8.4 | 6.7 | 10.0 | 11.2 | 7.5 | 6.4 |
| total olefins | 62.2 | 78.1 | 83.6 | 69.2 | 83.2 | 87.7 | 62.8 | 79.9 | 84.0 |

EXAMPLE 6

Operation at high conversion using diluted methanol feed

In a continuous flow apparatus, a bed of about 1 ml of H-NU-3 from Example 1 having a particle size 500–700μ was activated at 450° C. in air for 16 hours followed by 1 hours in nitrogen at 450° C. The catalyst was maintained at 450° C. and a mixture (%$^v$/v) of 60 methanol vapour+40 nitrogen was passed over it. The LHSV of methanol was 1.2, giving a methane conversion over 95%. The $C_1$–$C_4$ hydrocarbon analysis is given in Table 9: no liquid hydrocarbons were observed.

TABLE 9

| Time after start (min) | | 3 | 33 | 64 | 95 |
|---|---|---|---|---|---|
| % v/v | methane | 16.1 | 19.1 | 22.3 | 23.2 |
| | ethane | 3.2 | 3.5 | 3.2 | 2.8 |
| | ethene | 35.5 | 34.8 | 33.8 | 37.3 |
| | propane | 3.2 | 3.5 | 3.2 | 1.1 |
| | propene | 25.8 | 27.0 | 23.6 | 19.8 |
| | butenes | 16.1 | 12.2 | 14.0 | 19.8 |
| Total $C_2$ + $C_3$ olefins | | 61.3 | 61.8 | 57.4 | 57.1 |

EXAMPLE 7

Conversion using zeolite of higher alkali content

The zeolite preparation of Example 1 was modified by increasing the synthesis time to 5 days and effecting less complete ion exchange. The product has the following composition ignoring hydrogen 0.18 $Na_2O.Al_2O_3$.43 $SiO_2$ but including 18% $^w$/w alpha quartz as impurity. (0.18 $Na_2O$ corresponds to 82% replacement of the sodium at acid sites by hydrogen).

This sample was tested as described in Example 6. At an LHSV of 1.1 the methanol conversion was over 95% and no liquid hydrocarbon product as observed. The composition of the $C_1$–$C_4$ hydrocarbon product is given in Table 10.

TABLE 10

| Time from start (min) | | 33 | 64 | 95 |
|---|---|---|---|---|
| % v/v | methane | 15.9 | 20.2 | 21.7 |
| | ethane | 3.2 | 4.7 | 3.1 |
| | ethene | 34.1 | 35.7 | 43.4 |
| | propane | 5.6 | 3.9 | 2.3 |
| | propene | 29.4 | 22.5 | 17.1 |
| | butenes | 11.9 | 13.1 | 12.4 |
| Total $C_2$ + $C_3$ olefins | | 63.5 | 58.2 | 60.5 |

EXAMPLE 8

Use of sodium quinuclidinium NU-3 of lower silica/alumina ratio

The Nu-3 synthesis mixture had the following molar composition 5.85 $Na_2O.8.7$ $QI.Al_2O_3.30$ $SiO_2.315$ $H_2O$ Silica (131 g of KS 300) was dispersed in 427.6 g of an aqueous solution containing 15 g sodium aluminate and 23.6 g sodium hydroxide. The slurry was homogenised for 15 minutes at 90° C. and then N-methyl quinuclidinium iodide (146 g) was stirred in, and stirring was continued for 15 minutes. Finally the gel slurry was transferred to a 1 liter stainless steel stirred autoclave and reacted for 5 days at 180° C. The product was recovered and calcined as in Example 1 and had the following molar composition ignoring hydrogen 0.96 $Na_2O.Al_2O_3.21$ $SiO_2$ Conversion of methanol A sample of the uncalcined sodium quinuclidinium NU-3 prepared as above was calcined in air for 72 hours at 450° C., then slurry exchanged with 10 ml N.HCl per g of zeolite for 1 hour at 60° C., washed with 50 ml distilled water per g of zeolite and dried overnight at 120° C. The sample was activated and tested as in Example 6. At an LHSV of 1.2, the methanol conversion was over 90% in the first hour and about 50% in the second hour. No liquid hydrocarbon product was observed. Table 11 shows the $C_1$–$C_4$ hydrocarbon product composition.

TABLE 11

| Time after start (min) | | 32 | 64 | 95 |
|---|---|---|---|---|
| % v/v | methane | 18.2 | 13.1 | 15.0 |
| | ethane | 3.2 | 3.1 | 3.8 |
| | ethene | 15.3 | 19.3 | 51.3 |
| | propane | 5.6 | 2.5 | 1.3 |
| | propene | 34.1 | 21.7 | 15.0 |
| | butenes | 23.6 | 31.1 | 13.8 |
| Total $C_2$ – $C_3$ olefins | | 49.4 | 41.0 | 66.3 |

We claim:
1. A process for making an olefin containing 6 or fewer carbon atoms in the molecule by reacting over a catalyst a feedstock comprising an oxygenated hydrocarbon and recovering the olefin from the products of the reaction, the said catalyst comprising zeolite NU-3 as defined in Table 1 hereinbefore.

2. A process according to claim 1 in which in the NU-3 X is silicon, Y is aluminium and the number of mols of $SiO_2$ is in the range 10 to 300 per mol of $Al_2O_3$.

3. A process according to claim 1 in which in the NU-3 the alkali metal present after synthesis have been replaced by hydrogen ions to the extent of at least 10% of the acid sites.

4. A process according to claim 1 in which the NU-3 contains less than 2% w/w of quinuclidinium calculated as elemental carbon.

5. A process according to claim 1 in which the feedstock is methanol or dimethyl ether.

6. A process according to claim 1 in which the temperature is in the range 350°–450° C.